United States Patent [19]

Stocker et al.

[11] Patent Number: 5,187,102
[45] Date of Patent: Feb. 16, 1993

[54] INHIBITORS FOR THE ANTICOAGULANT PRETREATMENT OF BLOOD SAMPLES

[75] Inventors: Kurt F. Stocker, Aesch, Switzerland; Ernst Wenzel, Wien, Austria

[73] Assignee: Pentapharm AG, Basel, Switzerland

[21] Appl. No.: 654,706

[22] Filed: Feb. 13, 1991

[30] Foreign Application Priority Data

Feb. 14, 1990 [CH] Switzerland .................. 00478/90

[51] Int. Cl.$^5$ .................. G01N 33/86; A61K 31/445
[52] U.S. Cl. .................. 436/69; 514/315; 514/822
[58] Field of Search .................. 436/67, 69; 435/13; 514/315, 2, 822; 530/380; 546/184

[56] References Cited

FOREIGN PATENT DOCUMENTS 7900638  6/1979  Sweden .

OTHER PUBLICATIONS

Chem. Abst. 111(9):70596h, 1989.
Chem. Abst. 105(3):18089g, 1986.
Chem. Abst. 107:146680w, 1987.
Merch Index, 9th ed. no 4593, 1976.
Die Pharmazie, Band 43, Nr. 11, Nov. 1988, Seiten 737-744, VEB Verlag Volk und Gesundheit, Berlin, DE; P. Walsmann: "Uber den Einsatz des spezifischen Thrombininhibitors Hirudin fur diagnostische und biochemische Untersuchungen".
De Pharmazie, Band 41, Nr. 1, Juli 1986, Seite 509, VEB Verlag volk und Gesundheit, Berlin, DE; H. Horn et al., "Synthese von Nalpha-(2-Naphthylsulfonyl-glycyl)-4-aminomethyl-und-4-amino-phenylalanin-piperidid als Thrombininhibitoren".

*Primary Examiner*—John W. Rollins
*Attorney, Agent, or Firm*—Pennie & Edmonds

[57] ABSTRACT

Meizothrombin- and thrombin-inhibiting inhibitors which do not bind bivalent cations and which are used for the anticoagulant pretreatment of blood samples to be used in the determination of the functions and/or changes of state of blood cells and blood corpuscles, and for treating devices and receptacles used for taking and/or receiving blood samples.

20 Claims, 3 Drawing Sheets

INHIBITORS FOR THE ANTICOAGULANT PRETREATMENT OF BLOOD SAMPLES

Background

Cells and corpuscles that are suspended in the blood liquid (plasma) fulfill various vital functions. Indeed, white blood corpuscles (leukocytes) fulfill multiple purposes in the defense against infection. Red blood corpuscles (erythrocytes) act as vehicles for the transport of oxygen and carbon dioxide, and blood platelets (thrombocytes) serve haemostasis and repair of injured blood vessels. The detection of deviations from the norm concerning the number, aspect, properties and functions of these cells and corpuscles allows the diagnosis and characterization of existing diseases or inherited anomalies. Therefore, the determination of the functions and changes of state of blood cells and corpuscles or more specifically the measurement of meizothrombin- and thrombin-independent functions and properties of those cells, (abbreviated "FSBC determinations" in the following) has a considerable diagnostic significance. Most often performed FSBC determinations are blood or erythrocyte sedimentation rate, erythrocyte deformability, platelet aggregation, platelet adhesivity and release of biologically active substances from blood platelets, and furthermore various cytochemical tests for determining leukocyte functions, such as the peroxidase reaction or the nitroblue tetrazolium test.

However, these FSBC determinations are impeded by the spontaneous coagulability of blood. Indeed, through contact of leaking blood with a foreign surface, blood coagulation factors that are present in plasma in a labile state of rest are activated and undergo an interaction, leading first to the formation of the proteinase thrombin from an inactive precursor. Finally, thrombin causes the conversion of the colloidally dissolved plasma protein fibrinogen into gelated fibrin; blood thereby passes from the liquid to the coagulated, gelated state. Simultaneously, cells and corpuscles are entrapped in the fibrin clot and thus cannot be submitted to FSBC determinations anymore. Therefore, to perform such determinations in blood, its coagulability has to be inhibited by adequate measures.

Since several reactions involved in blood coagulation only occur in the presence of calcium ions, the coagulability of blood can be totally supressed by removing calcium ions by means of ion exchangers, precipitation reagents, or complexing agents. As calcium-binding, anticoagulating additives which are often used in the taking of blood samples, sodium citrate, sodium-, potassium- or ammonium oxalate, sodium sulfate, salts of ethylene diamine tetraacetic acid, and mixtures thereof may be cited. However, calcium ion-binding or precipitating additives are suitable only in cases where the blood sample is to be used in a calcium-independent FSBC determination. FSBC determinations of calcium-dependent functions, such as adhesion, aggregation, or release reactions of blood platelets, or examinations of intracellular or plasmatic electrolyte concentrations, can only be performed with anticoagulants that do not modify the electrolyte and, in particular, the calcium ion concentration. Moreover, various cell and corpuscle functions in blood and plasma do not only depend on calcium ions, but also on other bivalent cations, such as magnesium, zinc, or coupper ions, which are bound by salts of ethylene diamine tetraacetic acid or other complexing agents used as blood anticoagulants. Magnesium ions are also precipitated by oxalate salts in the form of poorly soluble magnesium oxalate.

Since sodium oxalate or sodium citrate cannot inhibit a spontaneous platelet aggregation, an acidic, glucose-containing sodium citrate solution is usually used as the anticoagulant in the taking of blood samples for the production of platelet-rich plasma. Acidic citrate solutions, however, do not only stabilize blood platelets, but also generally exert an inhibiting effect on their functions and reduce their reactivity to chemical and physical stimuli.

In order to obtain rapid intermixing of anticoagulant with blood, a graduated receptacle is usually charged with the required volume of an anticoagulant solution and then filled with freshly taken venous blood up to the corresponding calibrating mark. When proceding in this way, however, the FSBC determinations can only be performed by diluting the blood sample. In order to exclude any influence of varying dilution effects on the determinations, it is essential to strictly keep the correct mixture ratio between blood and anticoagulant. However, a constant sample dilution cannot be reached if the adequate blood quantity corresponding to the standardized quantity of anticoagulant solution cannot be provided because of difficulties encountered in the taking of blood. This particularly applies when blood is taken from children. Moreover, the used anticoagulants used have to be available as isotonic solutions, since osmotic changes of the medium may strongly influence the properties and functions of blood cells and corpuscles. In the extreme case, hypotonicity of the medium, for example, may lead to a bursting of the erythrocytes, a so-called haemolysis. Besides, the calcium-binding anticoagulant solutions have to be of a nature such that the physiological pH value remains unchanged, because platelet functions in particular are strongly influenced by a decrease in the pH value.

Determining the blood sedimentation rate (BSR) in a blood sample consists of measuring the extent of the red blood cell sedimentation taking place within a given period of time as a result of the difference in density between blood liquid and cells. An increased BSR is the expression of an active disease process, such as an infection, a vascular disease or a cancerous disease. A reduced BSR is for example observed in cases of abnormally formed erythrocytes (sickle-cell anemia), of pathologically higher erythrocyte numbers (polycythemia), or of reduced fibrinogen levels (hypofibrinogenemia).

The BSR depends on the tendency of erythrocytes to aggregate and form roll-shaped lumps. This formation of rolls is determined by the properties of the erythrocytes themselves, by shearing forces, temperature, viscosity of blood plasma and by the action of bridging macromolecules. Under normal conditions, the electronegative charge of erythrocytes counteracts aggregation, and the normal BSR corresponds to the sedimentation of free, non-aggregated erythrocytes. Roll-shaped aggregation occurs when determined plasma proteins, such as fibrinogen, $\alpha$- and $\beta$-globulins, accumulate on the cell surface and weaken the electronegative charge of the erythrocytes which causes mutual repulsion. Cylindrical aggregates possess, with regard to their surface, a higher particle weight than free erythrocytes and, therefore, sediment more quickly.

The formation of soluble fibrin complexes in blood, induced by thrombin or thrombin-like enzymes, causes a drastically reduced BSR (Blättler et al., Thromb. Res. 4, 787, 1974). A detailed description of the BSR determination can be found in K.-G. v. Boroviczeny et al., Qualitätssicherung im Medizinischen Laboratorium, Springer-Verlag, Instand Schriftenreihe, Vol. 5, 553–572, 1987. All the methods described have the same disadvantage: the preparation of the blood sample requires solutions of anticoagulants which affect the plasma viscosity as well as the action of bridging macromolecules due to the dilution effect, thereby modifying the result of the BSR measurement (see H. Kiesewetter and H. Radtke: Die Blutsenkung: Ein altes klinisches Verfahren unter neuen Aspekten, Klin. Wochenschr. 61, 621–624, 1983). A mere 5% variation in mixture ratio of blood and anticoagulant produces, a 10% deviation in the value measured per hour.

Moreover, a significant source of error in FSBC determinations in anticoagulated blood samples lies in a possible microbial contamination of the anticoagulant solution. Any microbial contamination of the anticoagulant solution can be eliminated by charging in advance the tubes or syringes to be used for the taking of blood with anticoagulant solution, by packing these receptacles in a germ-impermeable manner and by sterilizing them. Such blood-taking devices that have been specially prepared for BSR determination are available from specialized suppliers; although they considerably simplify the performance of the determinations, they still involve the risk of a wrong mixture ratio of blood and anticoagulant. Besides, these blood-taking devices only allow one to perform calcium-independent FSBC determinations and only in diluted blood samples.

In order to eliminate the dilution effect of the pre-furnished anticoagulant solution in BSR determination, an attempt has been made to modify the method by filling the sample tubes with the anticoagulant oxalate solution and drying them at 60° C. to prevent dilution of the blood sample. However, anticoagulation of 1 ml of blood requires 20 mg of oxalate salts which, after drying, are present as relatively coarse particles that dissolve only slowly and only by adequate shaking. While shaking, the formation of air bubbles must be prevented, as they disturb the erythrocyte sedimentation and thus alter the result of the determination. The effects of this source of error depend on the individual mode of operation and can neither be completely eliminated nor standardized when using dried oxalate.

Moreover, the use of oxalate or citrate salts as anticoagulants leads to the formation of insoluble calcium salts that adhere to blood cells and corpuscles, the specific weight and surface structure of which are modified, thus influencing the various FSBC determinations. Additionally, calcium citrate and calcium oxalate can adsorb plasma proteins, whereby the BSR and the other FSBC determinations may be significantly altered.

An attempt has been made to do without liquid calcium ion-eliminating anticoagulants by coating the receptacles used for blood taking with heparin, a coagulation inhibitor which is effective at low concentration, and by drying them. Heparin is a mucopolysaccharide with a molecular weight of approx. 17,000 Dalton which, together with antithrombin III, a protein contained in blood plasma and having a molecular weight of 6,000 Dalton, forms a high molecular inhibitor complex which inhibits α-thrombin, the key enzyme of blood coagulation, and the clotting factors IXa, Xa, XIa and XIIa, thereby inhibiting the coagulation, but not a spontaneous viscosity modification of the blood sample. Therefore, heparin has proved to be unsuitable for performing a BSR determination according to Wintrobe (S. S. Raphael (ed.), Lynch's Medical Laboratory II, 3rd Edition, W. B. Saunders Co., Philadelphia, 1976). Heparin binds to platelet factor 4 (PF 4), which is released during thrombocyte aggregation and is thereafter inactivated. Due to this interaction, heparin cannot be used as a blood anti-coagulant in the determination of PF4 release. Moreover, heparin exerts a strong platelet-aggregating action and thus cannot be applied as an anticoagulant in the determination of platelet functions. Due to this aggregating action, which may vary according to the origin and the degree of purity of heparin, the latter is inadequate as an anticoagulant even in the microscopic or automatic counting of platelets in plasma. Heparin and calcium-complexing agents, such as ethylene diamine tetraacetic acid, reduce the platelet adhesivity and are consequently not suitable as anticoagulants in blood samples for platelet adhesivity determinations. In cytochemical colour reactions on leukocytes, the electronegatively charged heparin may lead to the undesired binding of colour reagents.

The level of antithrombin III, which is essential to the development of the coagulation-inhibiting action of heparin and which is present in sufficient quantities in the plasma of healthy test persons, is strongly decreased in case of various diseases such as liver cirrhosis, hepatitis, venous thrombosis, disseminated intravascular coagulation, and septicemia, or under various medications, e.g. when taking oral contraceptives, or in the presence of an inherited antithrombin III defect. In these cases, the anticoagulant action of heparin in the preparation of blood samples for analytical purposes may partially or completely fail.

DETAILED DESCRIPTION OF THE INVENTION

Figure 1:
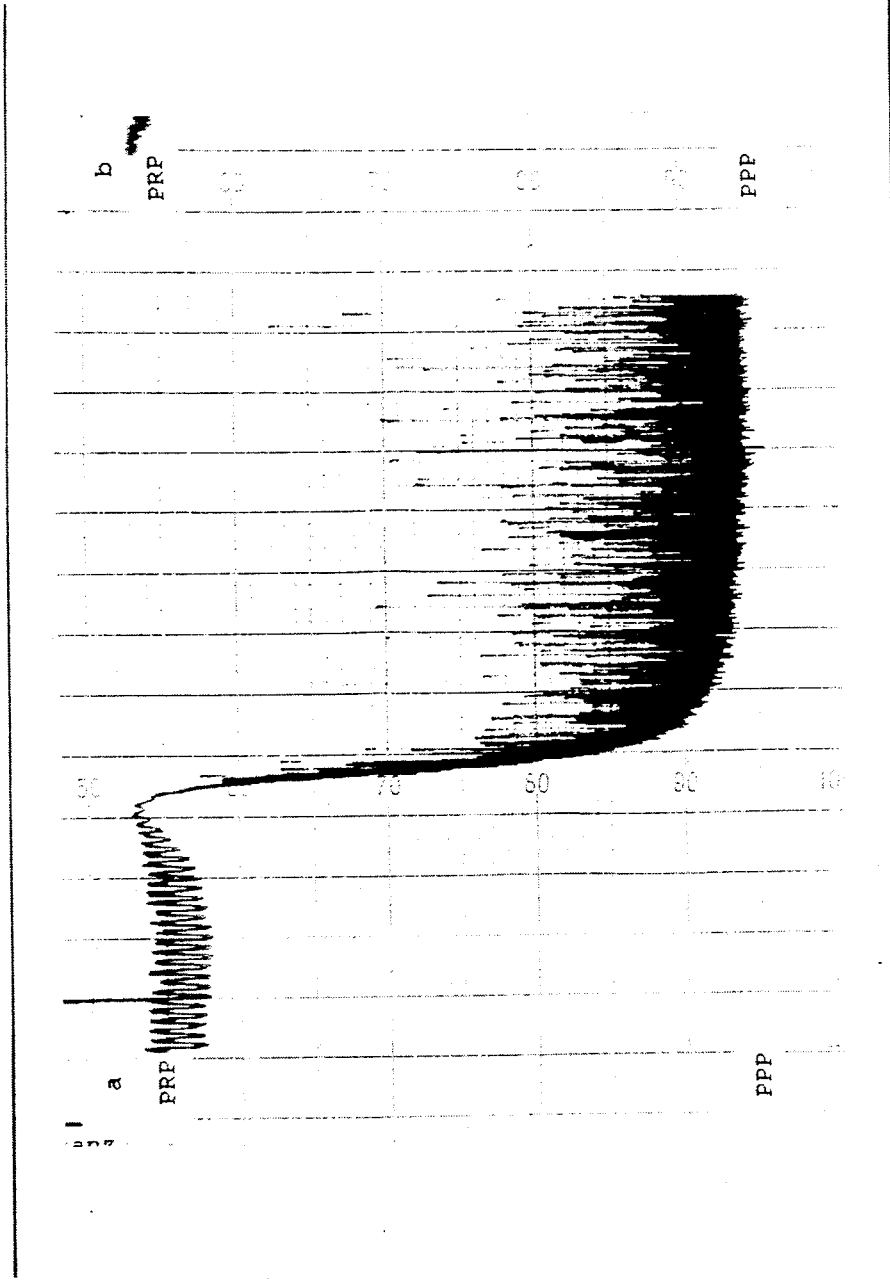
FIG. 1 is a graphical illustration of a photometrically recorded modification in the light absorbance of platelet-rich human plasma during thrombocyte aggregation induced by collagon.

It has now surprisingly been found that, contrary to heparin, the thrombin inhibitor hirudin from the medicinal leech *Hirudo medicinalis* is outstandingly suitable for the anticoagulant pretreatment of blood samples for FSBC determinations. Indeed, given in very weak concentrations, hirudin prevents the coagulation as well as a spontaneous change in viscosity of blood samples, it is highly soluble in water, and a multiple excess over the effectively required dose does not affect the cell and corpuscle functions. Besides, hirudin exerts no aggregating action on platelets and does not affect the thrombin-independent functions and the state of blood cells and corpuscles. Thus, hirudin has also been found to be useful in the determination of thrombocyte adhesivity, leukocyte adhesivity, and thrombocyte sedimentation and to constitute an effective blood anticoagulant, compatible with the most sensitive test systems that can be added to blood either in the form of a highly concentrated solution or in dry form. Consequently, hirudin is particularly well adapted to the dry coating of blood-taking and blood-testing devices, because it rapidly dissolves in the blood liquid and can be used in such high doses that even incomplete dissolution or insufficient intermixing of anticoagulant and blood sample as well as a volume inferior or superior to the sample quantity taken do not influence the result of the determination. Due to its high and specific inhibitory activity, hirudin is also particularly appropriate for the application of a soluble anticoagulant layer to microsedimentation tubes which are used to determine the BSR in capillary blood and which, because of their small lumen, only offer a very limited adsorption surface for the anticoagulant. Contrary to heparin, which may not only trigger the aggregation of platelets but also inhibit or potentiate the platelet aggregation caused by stimulating agents, hirudin does not affect thrombin-independent thrombocyte functions. Unlike heparin, hirudin does not bind platelet factor 4. Thus, hirudin is not inactivated by this protein which is released from platelets during their aggregation and viscous metamorphosis. Unlike heparin, the anticoagulant action of which can only develop in the case of a sufficient concentration of the cofactor antithrombin III in plasma, hirudin is an inhibitor which is totally independent of plasma cofactors and which can exert its action also in pathologically modified blood of patients suffering from most diseases. As a polypeptide, hirudin does not bind the basic dyestuffs which are used in the determination of leukocyte functions and which form insoluble complexes with the strongly acidic polysaccharide heparin. Finally, hirudin does not bind bivalent cations, in particular calcium, magnesium, zinc and copper ions. For this reason, the cell and corpuscle functions which depend on these ions are not disturbed by hirudin.

In comparison to the high molecular heparin-antithrombin III complex, hirudin, with a molecular weight of about 7,000 Dalton, is a small polypeptide that is secreted in several inhibitorily acting isoforms by the salivary gland of the medicinal leech. Eleven different molecular hirudin variants have so far been isolated from salivary glands of medicinal leeches and characterized. The complete amino acid sequence of the quantitatively predominant variant HV-1 has been elucidated. As a structural particularity of HV-1, a sulfated tyrosine group has been determined in position 63. As for the other natural hirudin variants, their structure has been partially elucidated and the natural occurrence of sulfated as well as of non-sulfated hirudin variants could be demonstrated. A detailed description of natural and, recombinant hirudins is to be found in F. Markwardt, Development of hirudin as an antithrombotic agent, Semin. in Thromb. Haemost. 15, 269–282, 1989. Hirudin inhibits α-thrombin and, as a low-molecular, mobile inhibitor, also its enzymatically active precursor meizothrombin which is not inhibited by the high-molecular heparin-antithrombin III complex. Since a chemical or enzymatic desulfatization of hirudin does not affect its inhibitory action, recombinant desulfatohirudin also constitutes a fully effective thrombin inhibitor.

It was furthermore found that not only hirudin obtained from medicinal leeches, but also hirudin obtained from microorganisms the genome of which was recombinated with the hirudin-coding gene, is useful as well in the anticoagulating pretreatment of blood samples for FSBC determinations. It was finally found that low molecular, synthetic thrombin and meizothrombin inhibitors, such as Nα-(2-naphthylsulfonylglycyl)-D,L-amidinophenylalanine piperidide (abbreviated NAPAP), serve the same purpose.

The present invention relates to a meizothrombin- and thrombin-inhibiting inhibitor which does not bind bivalent cations and which is useful in the anticoagulant pretreatment of blood samples to be used in the determination of the functions and changes of state of blood cells and corpuscles.

The inhibitor of the invention consists of hirudin or desulfatohirudin, or a compound having the following formula

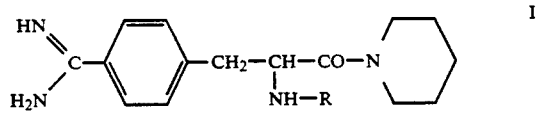

wherein R represents a toluenesulfonylglycyl, an α-naphthylsulfonylglycyl or a β-naphthylsulfonylglycyl group, or a mixture of hirudin or desulfatohirudin with a compound of formula I.

The compounds of formula I, known as such, present the same properties and the same advantages over heparin as hirudin.

As the hirudin species, either the polypeptide hirudin extracted from the medicinal leech H. medicinalis according e.g. to the method of Walsmann and Markwardt (Thromb. Res. 40, 563, 1985), or an r-hirudin or r-desulfatohirudin obtained from microorganisms by a recombinant technology according e.g. to the method of J. Dodt et al. (FEBS Lett. 202, 373, 1986) can be used.

The inhibitor of the invention can be used for example in the following determinations and investigations:

Determination of aggregation, sedimentation and deformability of erythrocytes.

Investigation of the adhesivity and of the cytochemical and immunological properties of leukocytes.

Investigation of the adhesion, aggregation and release reactions of thrombocytes.

The devices and receptacles for taking and collecting blood samples to be used in the determination of functions and changes of state of blood cells and other blood corpuscles, are treated or coated with the inhibitor of the invention. Tubes, syringes, capillaries, ampules, pipettes, microscopy slides, and microtiter plates made of glass, plastic or metal may be cited as examples of such devices and receptacles.

Thus, the present invention also relates to devices and/or receptacles for taking and collecting blood samples to be used in the determination of functions and changes of state of blood cells and other blood corpuscles, the said devices and receptacles being characterized by the fact that they are treated or charged with the inhibitor of the invention.

The charging of devices or receptacles with the inhibitor can be carried out by applying or introducing the powdered lyophilized or dried inhibitor, conveniently mixed with an inert carrier and dosed as to weight or volume, to or into the device or receptacle, or by filling with, spraying on or spraying in the inhibitor in the form of a solution and then drying the device or receptacle.

The three enclosed drawings 1 to 3 are diagrams showing the photometrically recorded modifications in the light absorbance of platelet-rich human plasma during thrombocyte aggregation induced by three different stimulators. In diagrams 1 to 3, the time (X axis) is plotted against the modifications in light absorbance (Y axis).

EXAMPLE 1

Blood-collecting plastic tubes having a capacity of 3 ml were provided with a calibration mark at a volume of 2 ml. Each tube was charged, by means of a pipette, with 0.1 ml of an aqueous solution containing 6000 antithrombin units (ATU) of r-hirudin per ml, and subsequently the tubes were vacuum-dried at 50°–60° C. The thus pretreated tubes were used for taking samples of 2 ml venous blood each. The blood contained in these pretreated tubes remained uncoagulated during at least 8 hours, i.e. a period of time sufficient for carrying out the determination of the blood sedimentation rate.

EXAMPLE 2

Blood-collecting plastic tubes having a capacity of 3 ml were provided with a calibration mark at a volume of 2 ml. Each tube was charged, by means of a pipette, with 0.1 ml of an aqueous NAPAP solution containing 2 μmoles of NAPAP per ml, and subsequently the tubes were vacuum-dried at 50°–60° C. The blood samples contained in these pretreated tubes remained uncoagulated during more than 8 hours.

EXAMPLE 3

Blood-collecting plastic tubes having a capacity of 3 ml were provided with a calibration mark at a volume of 2 ml. Each tube was charged, by means of a pipette, with 0.1 ml of a solution containing 300 ATU of r-hirudin and 1 μmole of NAPAP per ml, and subsequently the tubes were vacuum-dried at 50°–60° C. The blood samples contained in these pretreated tubes remained uncoagulated during more than 8 hours.

EXAMPLE 4

Micromethod for determining the blood sedimentation rate

For carrying out a micromethod for determining the blood sedimentation rate, glass capillaries with a 150-mm length and 1-mm inside diameter were provided with a calibration mark at a height of 100 mm, measured from the bottom, and pretreated with an aqueous solution containing 5 μmoles of NAPAP, 6000 ATU of r-hirudin and 50 μl of glycerin per ml by sucking the anticoagulant solution up to the calibration mark and then allowing the solution to flow out again. The capillaries were then vacuum-dried at 50°–60° C. Blood taken from a fingertip and sucked into the pretreated capillaries remained uncoagulated during more than 8 hours. The values of the blood sedimentation rates determined on 3 normal persons by means of these capillaries amounted to 5/9, 3/7 and 9/20 mm per 1 and 2 hours, respectively.

EXAMPLE 5

Nitroblue tetrazolium (NBT) reaction

Nitroblue tetrazolium is a pale yellow dye which, after absorption by defined neutrophilic cells, is decomposed to formazan. Formazan appears as a blue-black precipitate in the cytoplasm of these neutrophilic cells. Normally, less than 10% of these neutrophilic cells absorb this dye. A surprising increase in the dye absorption has been observed in patients with bacterial infections, while a low or normal number of NBT-positive neutrophilic leukocytes was found in the presence of viral or fungal infections. 30 Venous blood taken in blood-taking tubes according to example 1 was centrifuged for 8 minutes at 1500 × g. The leukocyte-containing intermediate layer between the erythrocyte zone and the plasma zone was collected by means of a plastic pipette and incubated for 30 minutes at 37° C. in a plastic test tube with nitroblue tetrazolium reagent (0.2% NBT in phosphate buffer pH 7.2). After termination of the reaction, cell samples were smeared on microscopy slides, fixed with methanol, dried, and stained for 2 minutes with safranin. The smears were analyzed under the microscope at a 1000-fold enlargement, whereby 100 neutrophilic cells were examined as to their staining by the NBT reaction product formazan and the percentage of NBT-positive cells was then calculated. In three normal blood donors, 6.2%, 5.7% and 8.9%, respectively, of NBT-positive cells were found.

EXAMPLE 6

Measurement of platelet aggregation

Figure 2:
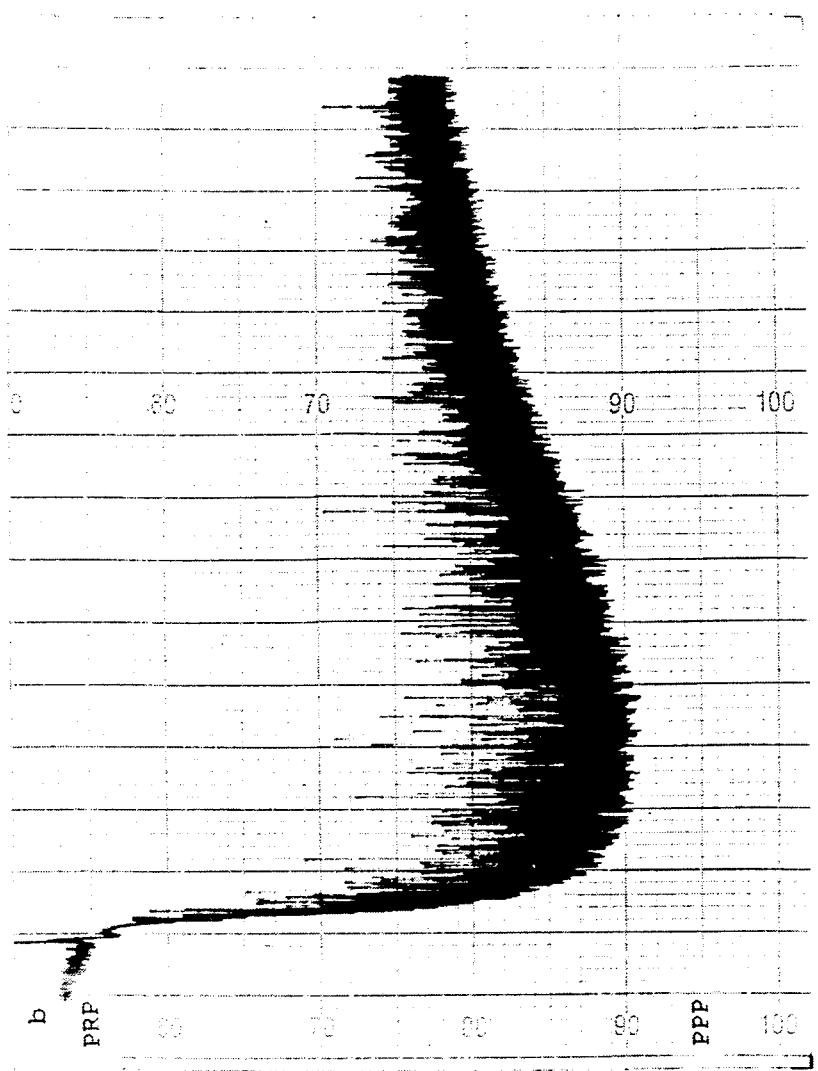
FIG. 2 is a graphical illustration of a photometrically recorded modification in the light absorbance of platelet-rich human plasma during thrombocyte aggregation induced by thrombocytin.
Figure 3:
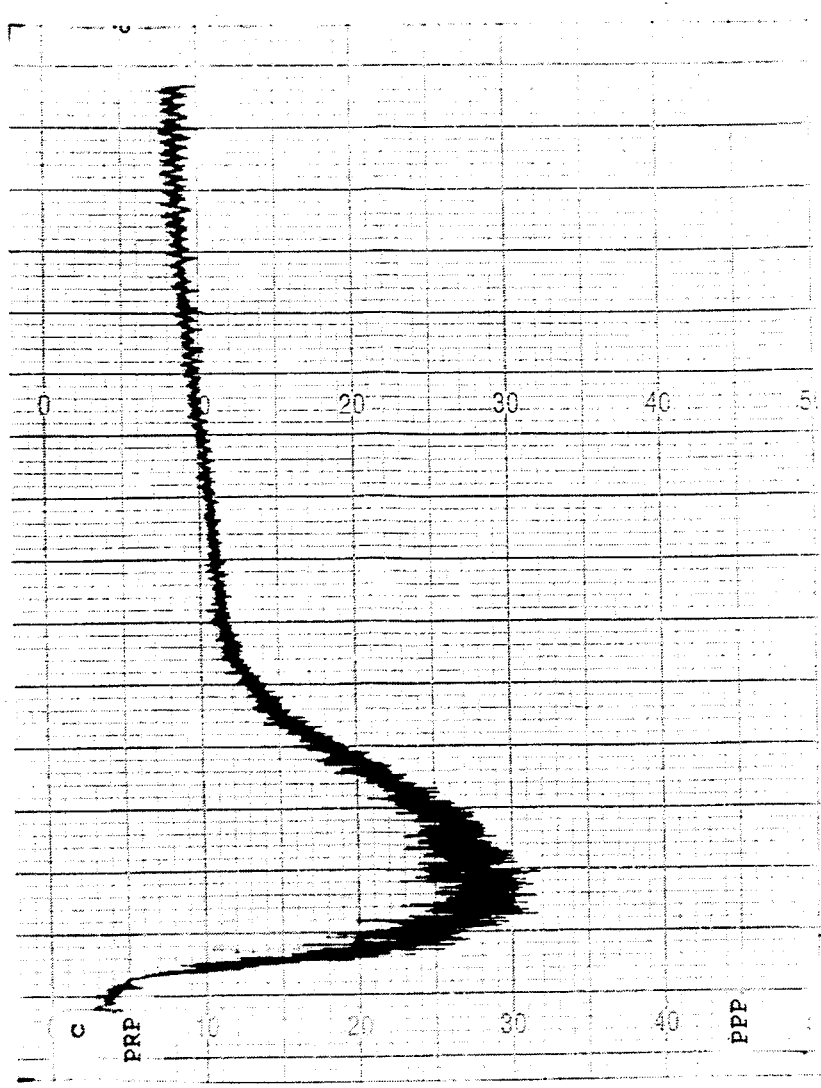
FIG. 3 is a graphical illustration of a photometrically recorded modification in the light absorbance of platelet-rich human plasma during thrombocyte aggregation induced by adenosinediphosphoric acid.

Polypropylene centrifuge tubes having a capacity of 15 ml and a calibration mark at a volume of 10 ml were each charged with 0.2 ml of an aqueous solution containing 30,000 ATU of r-hirudin per ml by means of a pipette and subjected to lyophilization. Freshly taken venous blood was added to these pretreated tubes up to the calibration mark. The tubes were closed with a plastic sheet and cautiously tilted five times by 90° in order to obtain good intermixing of blood and hirudin. After an 8-minute centrifugation at 1000 × g, the supernatant, platelet-rich plasma was removed with a plastic pipette and collected in a plastic tube. The platelet aggregation causing a decrease in light absorbance was photometrically measured on this platelet-rich hirudin plasma in a magnetically stirred cuvette after addition of collagen (a) (see FIG. 1), thrombocytin (b) (see FIG. 2) and adenosinediphosphoric acid (c) (see FIG. 3).

EXAMPLE 7

Measurement of clot retraction

Heat-sterilized test tubes having a diameter of 9.75 mm were each charged each with 0.6 ml of platelet-rich hirudin plasma according to example 6 by means of a pipette. Successively, 0.2 ml of a solution of adenosinediphosphate (ADP) in physiological sodium chloride solution or 0.2 ml of physiological sodium chloride solution (blank), respectively, and then 0.1 ml of aqueous batroxobin solution containing 20 BU of batroxobin per ml were added to each tube. The samples were kept motionless in a water bath at 37° C. for 2 hours; afterwards, the extruded serum was separated from the retracted clot and its volume was measured by means of a μl syringe. The clot retraction was calculated in percent from the initial clot volume and from the measured serum volume. It amounted to 0 for the blank test and to 94% for the test performed with ADP.

EXAMPLE 8

Determination of the blood sedimentation rate in case of anticoagulant overdose

Blood-taking plastic tubes were pretreated according to examples 1 to 3 with hirudin (H), NAPAP (N) and hirudin plus NAPAP (HN), respectively, and provided with a calibration mark each at a volume of 2 and 1.5 ml. For comparison purposes, commercial blood-taking tubes having a calibration mark at 2 ml and coated with citrate solution (C) were provided with an additional calibration mark at a volume of 1.5 ml. Thus, four types of tubes different with regard to the anticoagulant were obtained (H, N, HN and C). Eight blood samples each were taken from volunteering blood donors and added to the four types of tubes. Each type of tube was filled with venous blood from each volunteer on the one hand up to the nominal volume of 2 ml and on the other hand up to the minimal volume of 1.5 ml. The citrated tubes which were filled with a insufficient blood volume showed much too low BSR values as compared to the citrated tubes provided with the nominal volume, while in all other blood samples collected with any of the tube types H, N and HN the BSR values found did not significantly differ from one volunteer to another based on the collected blood volume.

TABLE I

| Volume | Blood sedimentation rate (mm/hour) | | | |
| --- | --- | --- | --- | --- |
| | H | N | HN | C |
| 2 ml | 8 ± 6.7 | 8 ± 6.2 | 7 ± 6.2 | 7 ± 6.5 |
| 1.5 ml | 8 ± 6.8 | 7 ± 6.4 | 8 ± 6.4 | 5 ± 4.3 |

We claim:

1. A method for determining meizothrombin- and thrombin-independent functions and properties of blood cells which comprises treating a blood sample with a meizothrombin and thrombin inhibitor which does not bind bivalent cations, and measuring the meizothrombin- and thrombin-independent functions and properties of blood cells in the blood sample.

2. The method of claim 1 wherein said inhibitor comprises hirudin or desulfatohirudin.

3. The method of claim 2 which further comprises measuring aggregation, sedimentation, and deformability of erythrocytes in the blood sample.

4. The method of claim 2 which further comprises measuring adhesivity of and cytochemical and immunological properties of leukocytes in the blood sample.

5. The method of claim 2 which further comprises measuring aggregation and release reactions of thrombocytes in the blood sample.

6. The method of claim 1 wherein said inhibitor comprises a compound having the following formula

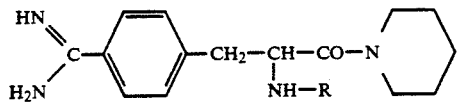

wherein R represents a toluenesulfonylglycyl, an α-naphthylsulfonylglycyl or a β-napthylsulfonylglycyl group.

7. The method of claim 6 which further comprises measuring aggregation, sedimentation, and deformability of erythrocytes in the blood sample.

8. The method of claim 6 which further comprises measuring adhesivity of and cytochemical and immunological properties of leukocytes in the blood sample.

9. The method of claim 6 which further comprises measuring aggregation and release reactions of thrombocytes in the blood sample.

10. The method of claim 1 wherein said inhibitor comprises a mixture of hirudin or desulfatohirudin with a compound of formula I.

11. The method of claim 10 which further comprises measuring aggregation, sedimentation, and deformability of erythrocytes in the blood sample.

12. The method of claim 10 which further comprises measuring adhesivity of and cytochemical and immunological properties of leukocytes in the blood sample.

13. The method of claim 10 which further comprises measuring aggregation and release reactions of thrombocytes in the blood sample.

14. The method of claim 1 which further comprises measuring the aggregation, sedimentation, and deformability of erythrocytes in the blood sample.

15. The method of claim 1 which further comprises measuring adhesivity of and cytochemical and immunological properties of leukocytes in the blood sample.

16. The method of claim 1 which further comprises measuring aggregation and release reactions of thrombocytes in the blood sample.

17. A device or receptacle for taking or receiving blood samples for the measurement of meizothrombin- and thrombinindependent functions and properties of blood cells in the blood sample which is charged with a meizothrombin and thrombin inhibitor which does not bind bivalent cations.

18. The device or receptacle of claim 17, wherein the inhibitor comprises hirudin or desulfatohirudin.

19. The device of receptacle of claim 17, wherein the inhibitor comprises a compound having the following formula

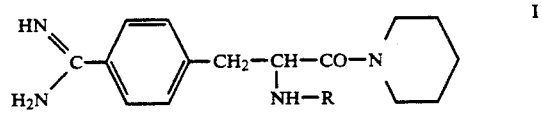

wherein R represents a toluenesulfonylglycycl, an α-naphthylsulfonylglycyl or a β-napthylsulfonylglycyl group.

20. The device or receptacle of claim 17, wherein the inhibitor comprises a mixture of hirudin or desulfatohirudin with a compound of formula I.

* * * * *